(12) United States Patent
Randall

(10) Patent No.: US 9,499,846 B2
(45) Date of Patent: Nov. 22, 2016

(54) METHOD FOR RECYCLING FLUE GAS

(71) Applicant: Mark Randall, Encinitas, CA (US)

(72) Inventor: Mark Randall, Encinitas, CA (US)

(*) Notice: Subject to any disclaimer, the term of this patent is extended or adjusted under 35 U.S.C. 154(b) by 0 days.

(21) Appl. No.: 14/529,075

(22) Filed: Oct. 30, 2014

(65) Prior Publication Data
US 2015/0159186 A1 Jun. 11, 2015

Related U.S. Application Data

(63) Continuation-in-part of application No. 14/102,423, filed on Dec. 10, 2013, now Pat. No. 9,345,208.

(51) Int. Cl.
C12P 7/64 (2006.01)
C12N 1/12 (2006.01)
F23G 7/06 (2006.01)

(52) U.S. Cl.
CPC .............. *C12P 7/6463* (2013.01); *C12N 1/12* (2013.01); *C12P 7/64* (2013.01); *F01N 2250/12* (2013.01); *F23G 7/06* (2013.01)

(58) Field of Classification Search
None
See application file for complete search history.

(56) References Cited

U.S. PATENT DOCUMENTS

| | | | |
|---|---|---|---|
| 4,253,271 A | 3/1981 | Raymond | |
| 5,151,347 A | 9/1992 | Delente et al. | |
| 6,274,067 B1 | 8/2001 | Oommen et al. | |
| 8,246,700 B1 | 8/2012 | Kutsin | |
| 8,333,944 B2 | 12/2012 | Constantz et al. | |
| 2006/0270036 A1* | 11/2006 | Goodwin | B01F 3/04269 435/395 |
| 2007/0048848 A1 | 3/2007 | Sears | |
| 2008/0178739 A1* | 7/2008 | Lewnard | B01D 53/84 95/186 |
| 2008/0220515 A1* | 9/2008 | McCall | C12M 21/02 435/292.1 |
| 2009/0294354 A1* | 12/2009 | Theodore | A01G 33/00 210/602 |
| 2010/0068779 A1 | 3/2010 | Wells et al. | |
| 2010/0233787 A1 | 9/2010 | Halachmi Katchanov | |
| 2010/0255458 A1* | 10/2010 | Kinkaid | C12M 21/02 435/3 |
| 2011/0277670 A1 | 11/2011 | Self et al. | |
| 2012/0119862 A1 | 5/2012 | Franklin et al. | |
| 2012/0244479 A1 | 9/2012 | Zhou et al. | |
| 2013/0125798 A1 | 5/2013 | Taylor | |
| 2013/0319059 A1 | 12/2013 | Chen et al. | |
| 2014/0093924 A1 | 4/2014 | Moll et al. | |

FOREIGN PATENT DOCUMENTS

WO 2012156588 A1 11/2012

OTHER PUBLICATIONS

Patent Cooperation Treaty, International Search Report for PCT/US2014/064857, Jan. 28, 2015, pp. 1-2.
Patent Cooperation Treaty, International Search Report for PCT/US2014/064865, Jan. 26, 2015, pp. 1-2.

* cited by examiner

*Primary Examiner* — Thane Underdahl
(74) *Attorney, Agent, or Firm* — Sheppard, Mullin, Richter & Hampton LLP

(57) ABSTRACT

A method for converting flue gas into useable bio-oil based compounds using algae includes mixing flue gas with water, infusing the mixture with a lipid trigger and nutrients, distributing the mixture into processing cells, exposing the mixture to light, promoting the algae to the top of the processing cells for harvest, skimming the algae from the surface of the water, and extracting bio-oil from the algae.

11 Claims, 13 Drawing Sheets

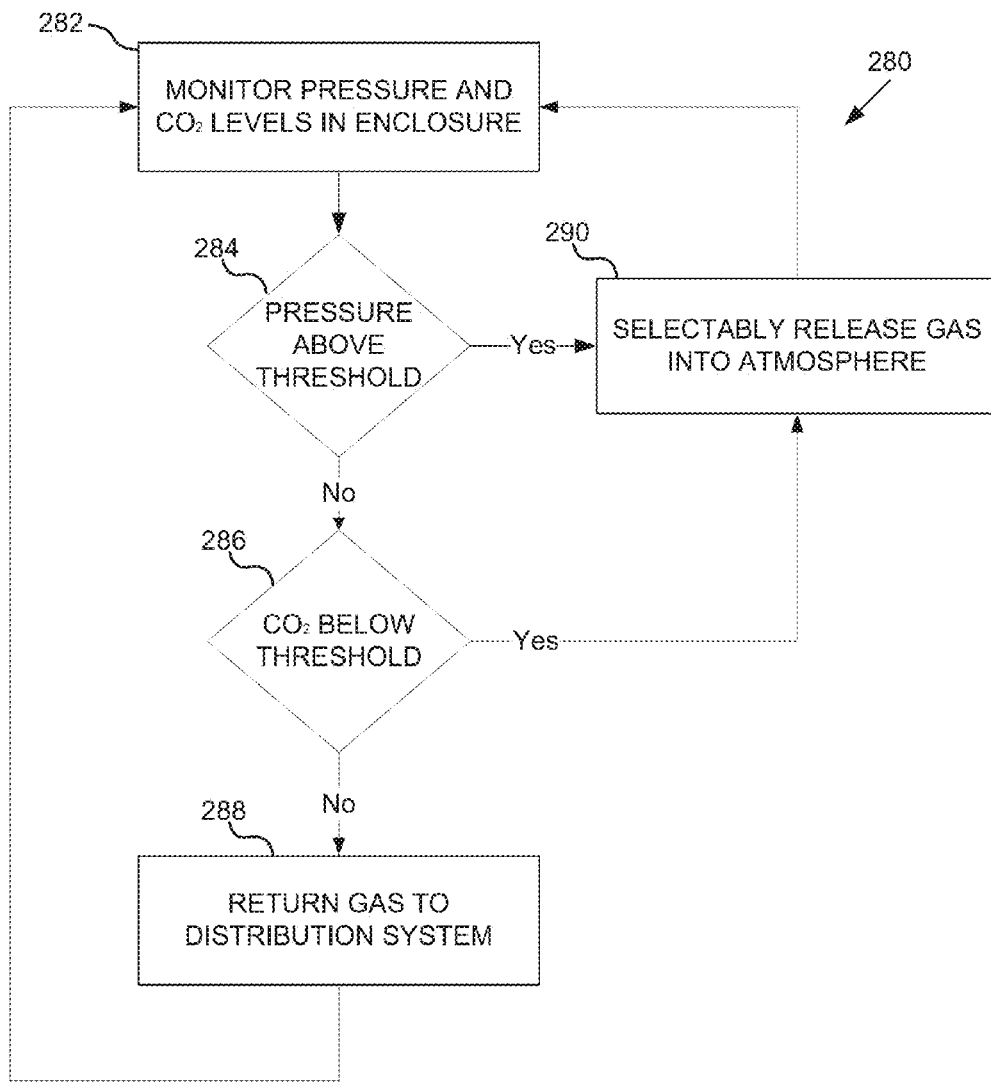
2H

METHOD FOR RECYCLING FLUE GAS

CROSS-REFERENCE TO RELATED APPLICATIONS

This application is a continuation-in-part of and claims the benefit of U.S. patent application Ser. No. 14/102,423, filed Dec. 10, 2013, titled "System for Recycling Flue Gas," the contents of which are incorporated herein by reference.

TECHNICAL FIELD

The disclosed technology relates generally to green energy. In particular, this application discloses a method for recycling flue gas.

BACKGROUND

Green energy sources have grown in importance over the last decade. Moreover, controlling the release of greenhouse gases, such as carbon dioxide, while still producing affordable and sustainable energy has become vitally important. Not only has an effort to reduce such emission been pushed to the forefront of modern research because of concerns over climate change, but has also become increasingly significant to industrial companies operating under heavy regulatory pressure. Indeed, many Western governments continue to pass increasingly more stringent regulations that effect companies that produce potentially harmful emissions (i.e. cap-and-trade). Thus, a need has emerged for economically viable methods to reduce harmful greenhouse gas emissions.

In particular, power plants that burn organic fuels such as coal, natural gas, wood, biomass or oil emit carbon dioxide ($CO_2$) and other harmful pollutants into the atmosphere during operation. Commonly used non-organic technologies to reduce these emissions are costly, inefficient, and not 100% effective. While organic emission reducing technologies can also be used, currently available technology has lacked the efficiency to gain commercial popularity. For example, microalgae naturally may be used to convert Carbon Di-Oxide ($CO_2$) into Oxygen ($O_2$). However, microalgae cultivation systems designed to reduce flue gas emissions generally lack the efficiency to be considered commercially viable. Moreover, incorporating such technologies into power plant operations adds cost with little benefit to the company, other than adhering to regulations. While microalgae can produce lipid-based oils, or bio-oils, as a byproduct creating a potential supplemental energy or revenue source for the company, currently available technology is incapable of producing sufficient levels of this biofuel to make the solution economically viable.

Recently, "lipid triggers" have been discovered that can dramatically boost bio-oil creation efficiency in microalgae. This discovery has made possible the prospect of sufficiently efficient, economical, and commercially viable flue gas emission reduction. In turn, a developing commercial need has emerged for a microalgae growing system and process that incorporates lipid trigger technology and that is capable of efficiently and economically reducing harmful flue gas emissions while producing sufficient levels of bio-oil in return.

BRIEF SUMMARY OF EMBODIMENTS

According to various embodiments of the disclosed technology, a method recycling flue gas is described. In particular, in accordance with some embodiments of the disclosed technology, a method for using nutrients non-transitory computer readable medium algae to efficiently convert flue gas into useable bio-oil, such as biofuel, bioplastic, biochemical, or other bio-oil based products, is described.

In some exemplary embodiments, the method comprises pre-processing flue gas, mixing flue gas with water, processing the gas-water mixture, distributing the gas-water mixture into a processing cell, stimulating algae growth, and harvesting algae. Processing flue gas may include adjusting the temperature of the flue gas to be conducive to algae growth. Mixing the flue gas may include introducing the flue gas into the water through a one-way valve, or backflow preventer such that water does not flow back into the flue gas exhaust of the producing plant. Processing the gas-water mixture may include infusing the mixture with nutrients for the algae, and/or with a lipid trigger to stimulate the algae to produce bio-oil at an increased rate. Distributing the flue gas may include controlling the release-rate of gas-water mixture into the processing cells. Stimulating the algae growth may include exposing the gas-water mixture to light at optimal wavelengths for algae growth and mixing or stirring the water to move algae and nutrients. Harvesting the algae may include promoting the algae to the top of the processing cell and skimming the surface water of the cell. For example, the algae may be promoted to the top of the processing cell by increasing the flow of gas-water mixture from bubblers at the bottom of the processing cell. In some embodiments, environmental variables are monitored with environmental sensors to enable tuning of temperatures, pressures, $CO_2$ levels, lipid trigger infusion, nutrients infusion, exhausting of gases from the system, or other environmental conditions.

In many embodiments, the method for processing flue gas is performed on a system for processing flue gas. The system for processing flue gas comprises a gas distribution system that pneumatically couples multiple watertight processing cells to flue gas exhaust from an industrial facility such as an energy plant. The multiple processing cells are filled with water and enclosed in an airtight enclosure. Each cell is isolated from the other cells to avoid cross-contamination. In addition, a bottom side, or floor of each cell may comprise a plurality of bubblers, wherein each bubbler pneumatically couples to the gas distribution system such that flue gas flowing from the industrial facility exhaust through the gas distribution system may be released into the cell. Further, each cell may comprise a plurality of light emitting columns, a movable grate, and multiple guide columns. The cell may be further configured such that: (i) the light emitting columns protrude downward from a top surface of the cell to provide a light source to effectively grow algae; (ii) the guide columns protrude upward from a bottom surface of the cell to guide the movement of the movable grate; and (iii) the grate slidably couples to the guide columns and further comprises a plurality of apertures shaped to match the profile and positioning of the light emitting columns and to enable sufficient water flow through the moving grate, and multiple ballast tanks to control movement of the grate.

In some embodiments, the light emitting columns may comprise light emitting diodes (LEDs), and in an exemplary embodiment, the LEDs emit light at optimal wavelengths for growing algae. In addition, the gas distribution system may further comprise a heat exchanger to reduce the temperature of hot flue gas exhaust to a temperature conducive to algae growth, and may also further comprise a backflow prevention system to stop water from the cells from flowing backwards through the gas distribution system and into the flue gas exhaust. The gas distribution system may also comprise a pH control system and/or a nutrient infusing system located between the backflow prevention system and the processing cells. Water will have flooded this location of the gas distribution system, allowing the flue gas to mix with water and enabling pH adjustment and nutrient addition. For example, the pH control system may use limestone to adjust the pH of the $CO_2$-rich water. The nutrients infusion system may be used to infuse a lipid trigger into the water. Lipid triggers stimulate the algae metabolism to store excess solar energy as lipids, thus increasing the production rate of bio-oil.

In other embodiments of the disclosure, the gas distribution system may further comprise a water holding tank positioned in front of the processing cells but after the backflow prevention system such that $CO_2$-rich flue gas and water can be mixed in holding tank.

In many embodiments of the disclosure, the enclosure further comprises a gas return system that pneumatically couples a top side of the enclosure to the gas distribution system, but that also comprises a pressure release valve to controllably release gas from the enclosure into the atmosphere. The gas return system may further comprise temperature, pressure, $CO_2$ level, and/or other sensors to monitor the environmental conditions of the enclosure. The data returned from these sensors may be used to manually or automatically adjust the pressure release valve such that more or less gas is returned to the gas distribution system. For example, if $CO_2$ readings are high, more gas may be returned. In addition, the temperature sensors, flow sensors, and other environmental monitoring sensors may be located on the gas distribution system, as well as in the processing cells themselves to monitor environmental conditions.

In some embodiments of the disclosure, an algae harvesting system may mechanically couple to the enclosure. The algae harvesting system may be a skimming device collects algae from a top surface of the water in each cell to collect and separate algae from the water. In these embodiments, algae is pushed to the top of any particular cell by increasing the amount of gas released by the cell's bubblers.

Other features and aspects of the technology described herein will become apparent from the following detailed description, taken in conjunction with the accompanying drawings, which illustrate, by way of example, the features in accordance with embodiments of the disclosed technology. The summary is not intended to limit the scope of this disclosure.

BRIEF DESCRIPTION OF THE DRAWINGS

The technology described herein, in accordance with one or more various embodiments, is described in detail with reference to the following figures. The drawings are provided for purposes of illustration only and merely depict typical or example embodiments. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 2H is a process flow diagram illustrating a method for exhausting or recycling gas from a flue gas processing system.

The figures are not intended to be exhaustive or to limit the technology to the precise form disclosed. It should be understood that the technology described herein can be practiced with modification and alteration, and that the invention be limited only by the claims and the equivalents thereof.

DETAILED DESCRIPTION OF THE EMBODIMENTS OF THE INVENTION

The technology described herein is directed towards a method for processing flue gas. In particular, in accordance with some embodiments, a method for recycling flue gas comprises: (i) processing input flue gas; (ii) mixing the flue gas with water to create a gas-water mixture; (iii) processing the gas-water mixture; (iv) distributing the gas-water mixture into a processing cell; (v) growing a $CO_2$-breathing and/or photosynthesis-capable organism (e.g., cyanobacteria, algae, plankton, diatoms, dinoflagellates, coccolithophores, or other $CO_2$-breathing and/or photosynthesis-capable organisms as are known in the art); (vi) harvesting the organism; and (vii) exhausting or recycling the exhaust gas. The disclosed method may be performed using a flue-gas recycling system.

From time-to-time, the technology is described herein in terms of example embodiments, environments and applications. Description in terms of these embodiments, environments and applications is provided to allow the various features and embodiments of the disclosed technology to be portrayed in the context of an exemplary scenario. After reading this description, it will become apparent to one of ordinary skill in the art how the technology can be implemented in different and alternative embodiments, environments and applications.

Figure 1:
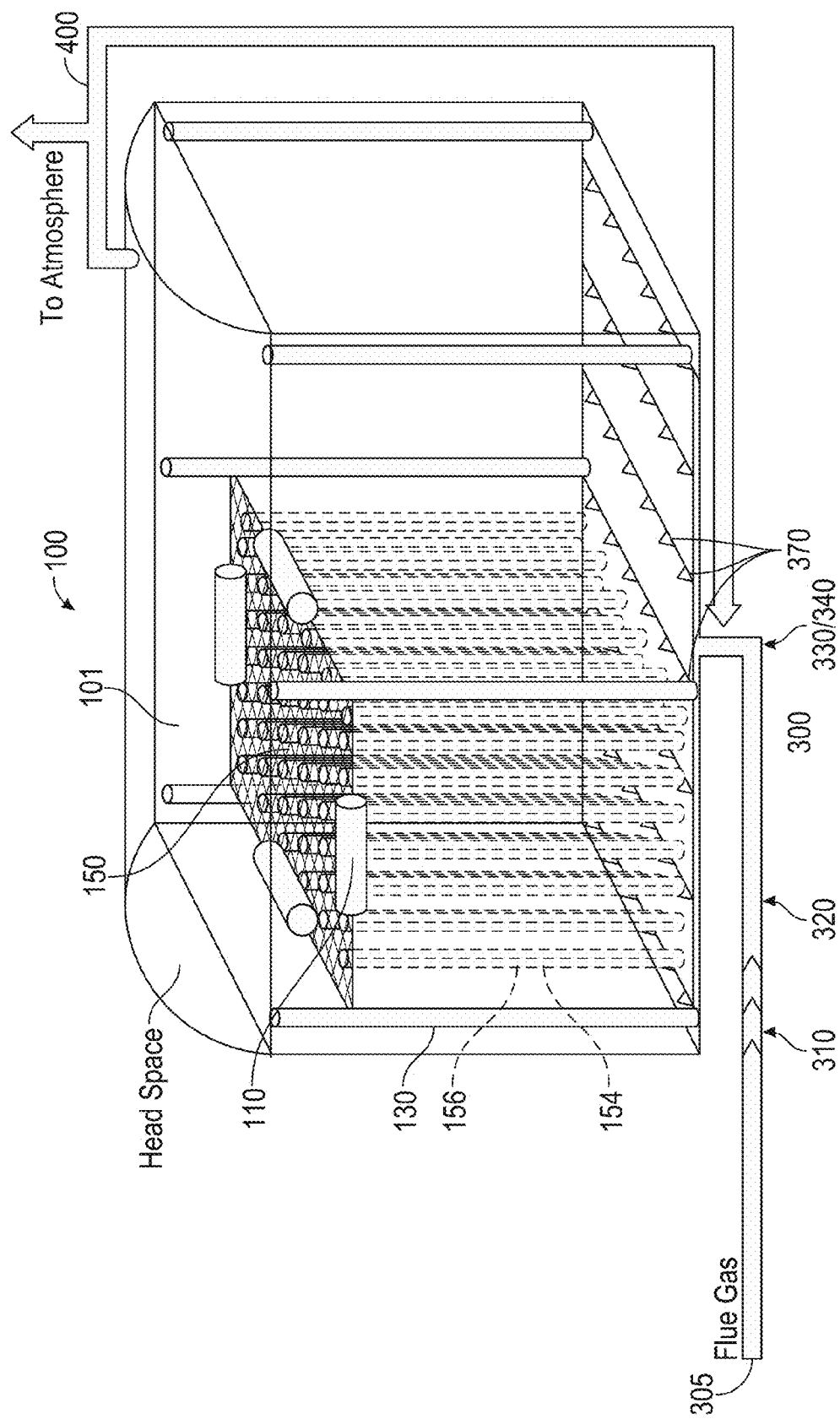
FIG. 1 illustrates a perspective view of a flue gas recycling system.

FIG. 1 is a perspective view illustrating a flue gas recycling system. Referring now to FIG. 1, a flue gas recycling system comprises a gas distribution system 200, an enclosure 100 comprising one or more processing cells 101, and a gas recovery system 400. A flue gas exhaust system from an industrial plant—for example a power plant—pneumatically couples to a gas distribution system 300 such that $CO_2$-rich flue gas 305 flows into the gas delivery system. Gas distribution system 300 pneumatically couples to a bottom surface of the enclosure through a plurality of bubblers 370. In some exemplary embodiments, a top surface of the enclosure is extended or bowed outward to create a cavity above the water surface in each processing cell 101 to collect accumulating gas percolating up or leaving solution from the water.

Still referring to FIG. 1, each cell 101 comprises a plurality of guide columns 130, a plurality of light emitting columns 156, and a moveable grate 150, the moveable grate comprising a plurality of ballast tanks 110 and a plurality of apertures. The guide columns 130 may protrude upward from a bottom surface of the cell, and the light columns 156 may protrude downward from a top surface of the cell. The moveable grate 150 may be shaped to fit the profile of the cell, and to slidably couple to the guide columns such that the grate may freely slide up or down within the cell cavity. In addition, the apertures in the grate are shaped to accept the profile of the light emitting columns 156 with sufficient clearance to also enable water to freely flow through the grate when it moves. Further, the apertures are positioned on the grate to match the orientation of the light emitting columns. As such, when the grate 150 is positioned in the cell cavity and coupled to the guide columns 130, the light columns 156 protruding from the top surface of the cell also fit through the apertures. As a result, the grate may move freely without interfering with or contacting the light columns.

In some embodiments, brushes or scrapes protrude from the inside edge of the apertures and contact the guide columns and/or light columns such that organisms and/or debris is scraped from the surface of the guide columns and/or light columns when the grate moves up or down.

Still referring to FIG. 1, each ballast tank 110 may be pneumatically coupled to the gas distribution system through a valve such that flue gas may be controllably be diverted into the tank. Each ballast tank may further comprise a hydraulic valve to controllably enable water to fill the tank. Thus, each tank may be controllably filled with either water, gas, or a combination thereof to control the buoyancy of the tank, and of the attached grate 150, in the water-filled cell 101. Accordingly, filling the ballast tanks with air will increase their buoyancy and cause the grate to float in an upward direction, and filling the ballast tanks with water will decrease their buoyancy, causing the grate to sink in a downward direction. These steps of filling the tank with gas and then with water may be repeated to cause the grate to move up and down repeatedly. This grate movement may be used to move and mix algae growing in the cell, as well as nutrients, to increase the probability that any particular algae specimen will have adequate and balanced exposure to nutrients and light.

Still referring to FIG. 1, the bottom surface of the enclosure 100 may also serve as the bottom surface of each cell 101. A subset of the plurality of bubblers may be dispersed throughout the bottom surface of each cell. Each bubbler 370 comprises a valve enabling $CO_2$ and nutrient rich gas or gas-solution to be controllably released into the cell 101. Under normal operation, the release of this gas or gas-solution may be controlled to create an optimal growing environment for the algae. As the algae grow, it also converts light energy into starch and lipids. These lipids are a type of oil that may be used as biofuel, bioplastic, biochemical, biocosmetic, or other bio-oil based products. When the algae has generated sufficient quantities of this bio-oil, it may be harvested by increasing the rate at which the bubblers release gas into the cell, thus pushing the algae to the surface of the water where it may be skimmed and collected.

In some embodiments, the light emitting columns comprise protective translucent tubes and an inner light emitting element 154. In an exemplary embodiment, this light emitting element comprises LEDs configured to emit light at optimal wavelengths conducive to algae growth. In some embodiments, these light emitting columns 156 protrude from the top surface of the cell and extend downward to approximately 1 meter from the bottom surface of the cell. Further, in some of these embodiments, the light emitting columns 156 are positioned in a grid pattern with the centers of each adjacent light emitting column separated by between 60 cm and 100 cm. However, these dimensions are exemplary, and other configurations with other light emitting column length, positioning, and spacing may be used depending on optimal growing conditions. For example, the light emitting columns may extend downward to between 5 meters and 0.1 meters of the bottom surface of the cell, and they may be positioned in multiple different orientations with the centers of adjacent light emitting columns spaced from between 0.1 meters to 5 meters apart. These special orientations and parameters may be optimized for particular algae strains.

In some embodiments, a processing cell may further comprise an auger system mechanically coupled to a bottom surface of the cell to remove particulate matter and other more dense materials that will sink instead of float to surface.

Several embodiments disclosed herein are directed towards systems and methods for growing algae. However, one of skill in the art would appreciate that the same systems and methods may also be utilized to efficiently grow and harvest other $CO_2$-breathing and/or photosynthesis-capable organisms, such as any type of cyanobacteria, plankton, diatoms, dinoflagellates, coccolithophores, or other $CO_2$-breathing and/or photosynthesis-capable organisms.

Figure 2A:
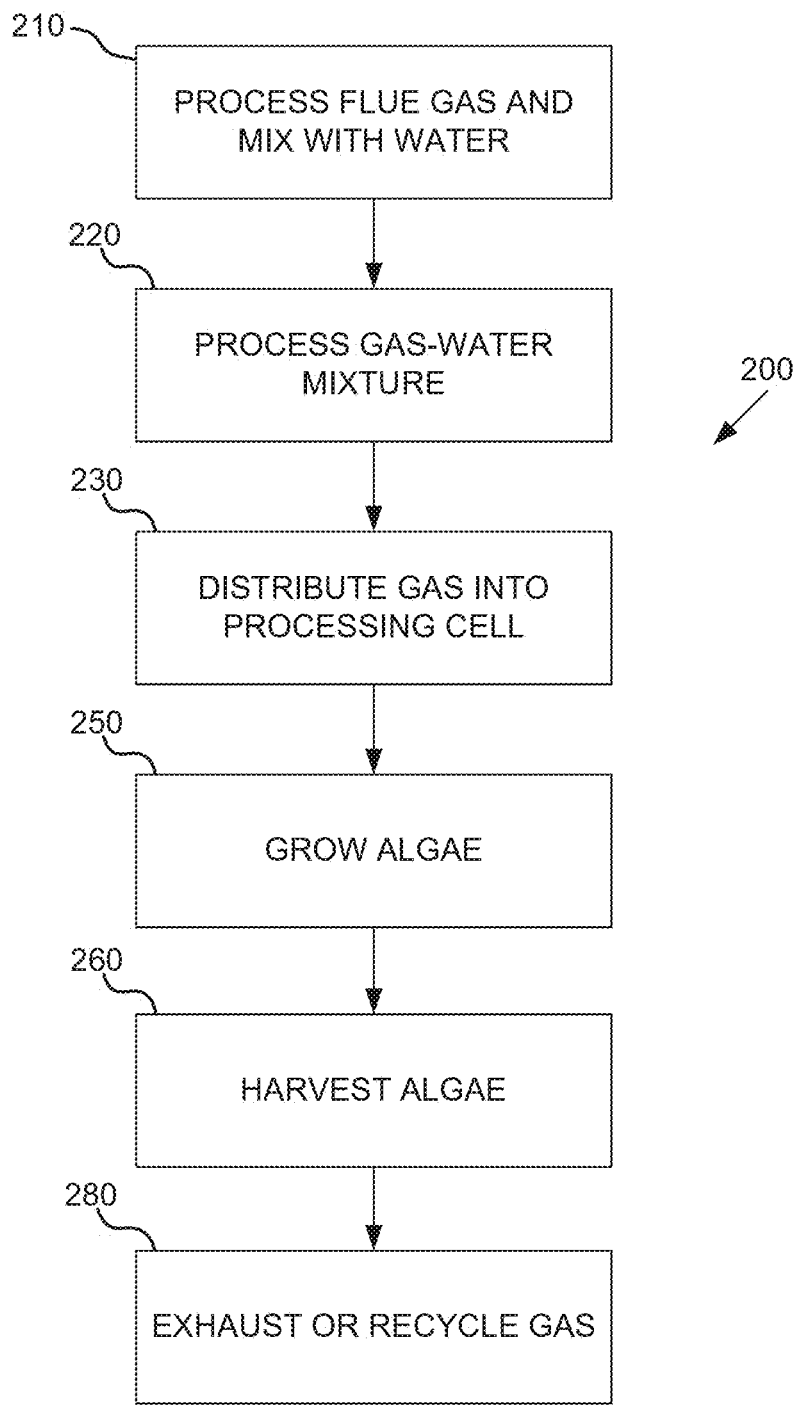
FIG. 2A is a process flow diagram illustrating a method for recycling flue gas.

FIG. 2A is a flow chart of a method for recycling flue gas. Referring now to FIG. 2A, a method for recycling flue gas, 200, comprises processing input gas and mixing with water at step 210 to create a gas-water mixture, processing the gas-water mixture at step 220; distributing the gas-water at step 230, growing algae at step 250, harvesting the algae at step 260, and exhausting or recycling exhaust gas at step 280. In many embodiments, method 200 may be performed using the system for recycling flue gas as illustrated in FIG. 1. For example, the processing flue gas and mixing with water of step 210 may include sub-steps performed by gas distribution system 300 and heat exchanger 310; the processing the gas-water mixture of step 220 may include sub-steps performed using nutrients infuser 330 and lipid trigger infuser 340; the distributing gas-water mixture into processing cell 101 of step 230 may include sub-steps performed using gas bubblers 370; the growing algae of step 250 may include sub-steps performed using light emitting columns 156 and moveable grate 150; the harvesting algae of step 260 may include sub-steps performed by a skimmer at the surface of cell 101; and the exhausting or recycling of exhaust gas of step 280 may include sub-steps performed using gas recovery system 400.

Figure 2B:
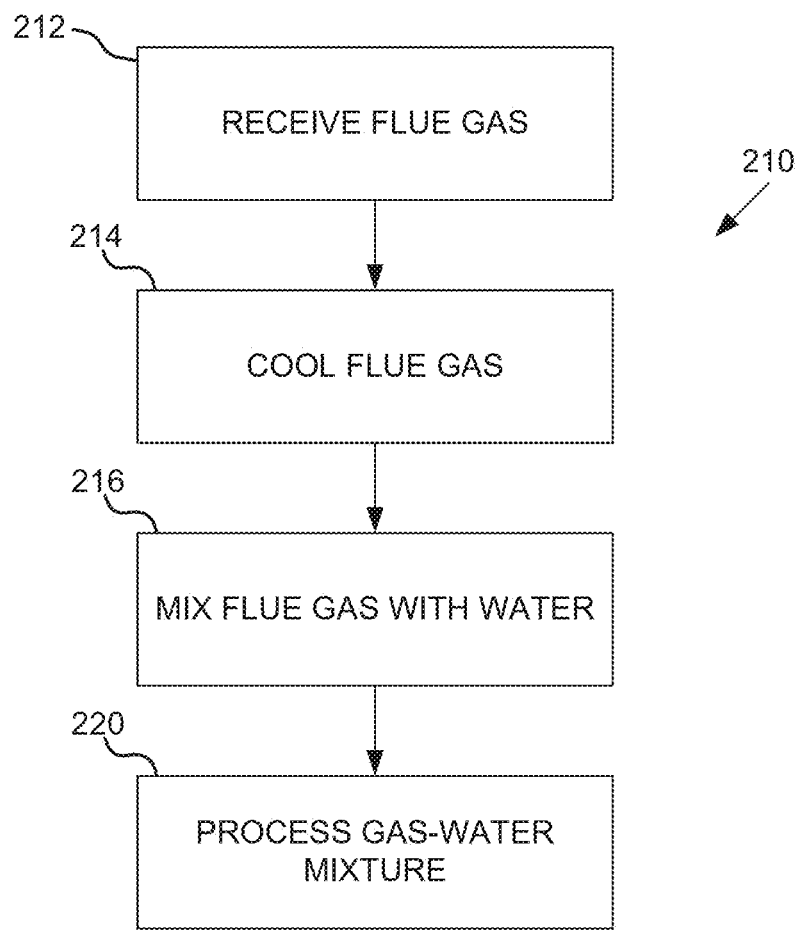
FIG. 2B is a process flow diagram illustrating a method for processing input gas as part of a process for recycling flue gas.

FIG. 2B is a process flow diagram illustrating a method for processing input gas and mixing with water. Referring now to FIG. 2B, a method for processing input gas comprises receiving input gas at step 212, cooling the input gas at step 214, mixing the input gas with water at step 216, and processing the gas-water mixture at step 220. In many embodiments, the cooling the input gas at step 214 may be performed by a heat exchanger 310 as illustrated in FIG. 1. Further, the mixing of the input gas with water may be performed by allowing flue gas to flow through a backflow prevention system 320 as illustrated in FIG. 1 wherein the backflow prevention system includes a one-way valve that allows gas to flow into water contained on the other side of the one-way valve.

Figure 2C:
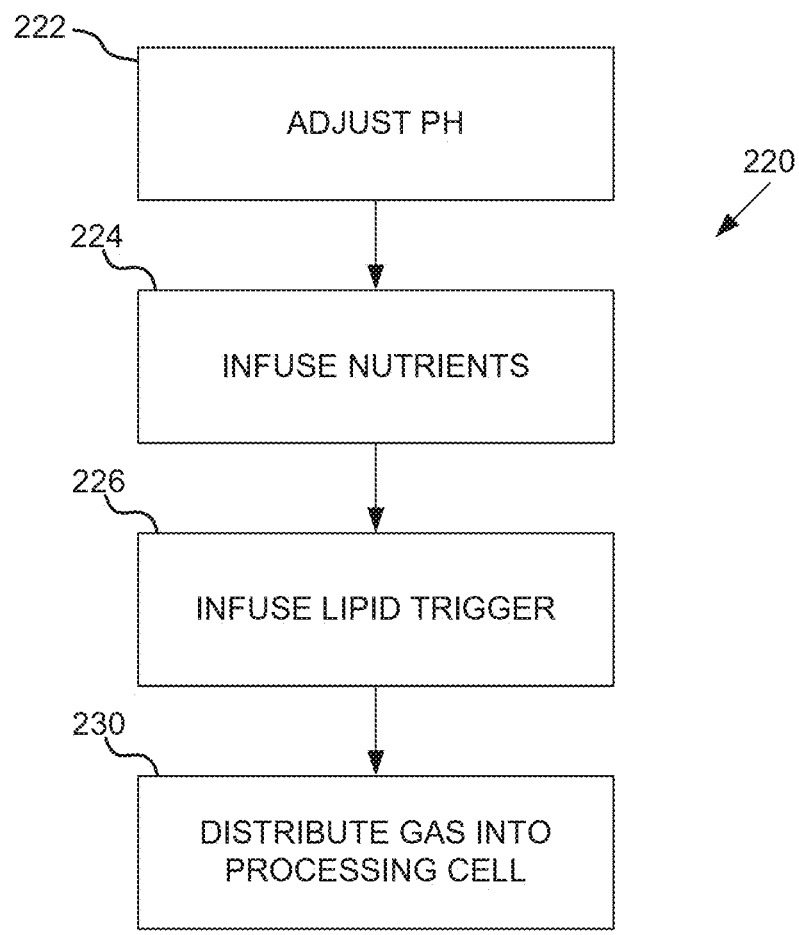
FIG. 2C is a process flow diagram illustrating a method for processing a gas-water mixture as part of a process for recycling flue gas.

FIG. 2C is a process flow diagram illustrating a method for processing a gas-water mixture as part of a process for recycling flue gas. Referring now to FIG. 2C, a method for processing a gas-water mixture comprises adjusting the pH at step 222, infusing nutrients at step 224, and infusing a lipid trigger at step 226. For example, as illustrated by FIG. 1, the adjusting of pH may include sub-steps performed by pH control system 330 and the infusing of nutrients and a lipid trigger may include sub-steps performed by nutrients infusion system 340.

Figure 2D:
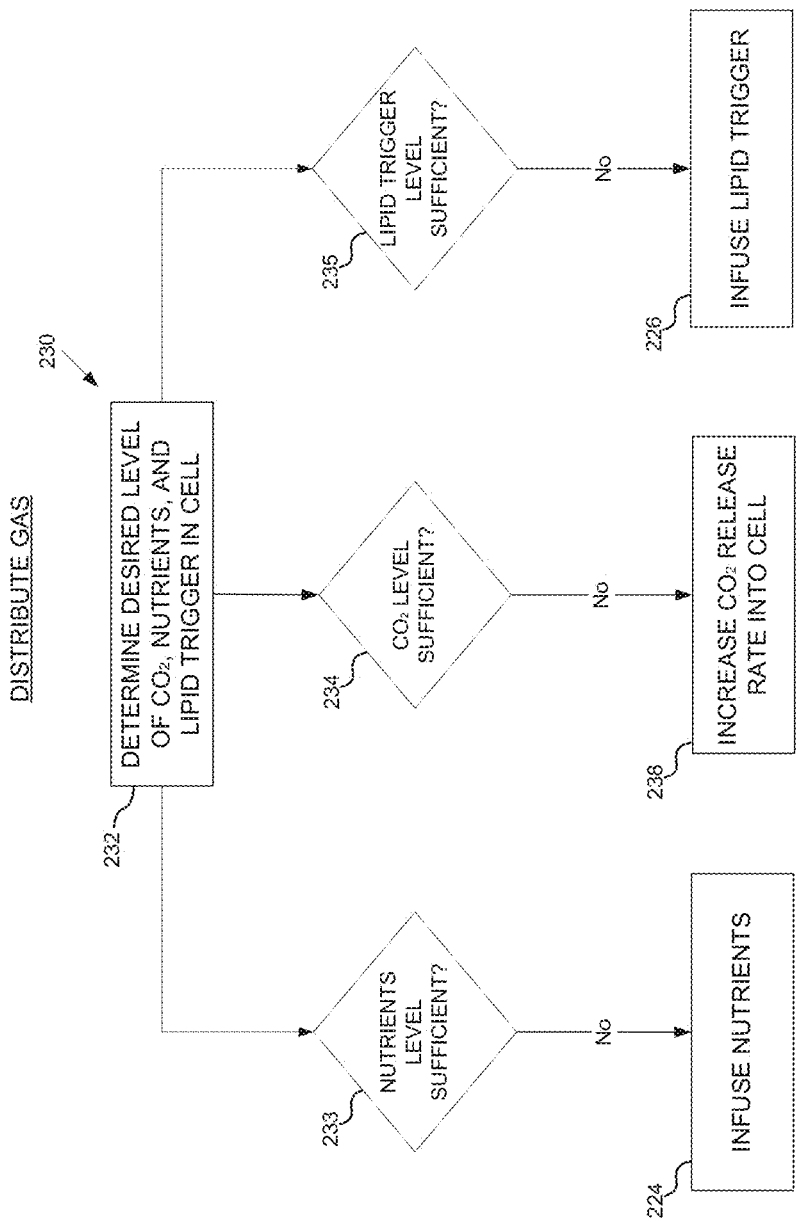
FIG. 2D is a process flow diagram illustrating a method for distributing gas into a processing cell as part of a process for recycling flue gas.

FIG. 2D is a process flow diagram illustrating a method for distributing gas into a processing cell as part of a process for recycling flue gas. Referring now to FIG. 2D, a method for distributing gas into a processing cell comprises determining desired levels of $CO_2$, nutrients, and lipid trigger at step 232, infusing more nutrients if the nutrients level is insufficient, infusing more lipid trigger if the lipid trigger is insufficient, and releasing more gas-water mixture into the cell if the $CO_2$ level is insufficient at step 238. For example, referring again to FIG. 1, the releasing of more gas-water mixture into processing cell 101 may include sub-steps performed by adjusting bubbler valves 370.

Figure 2E:
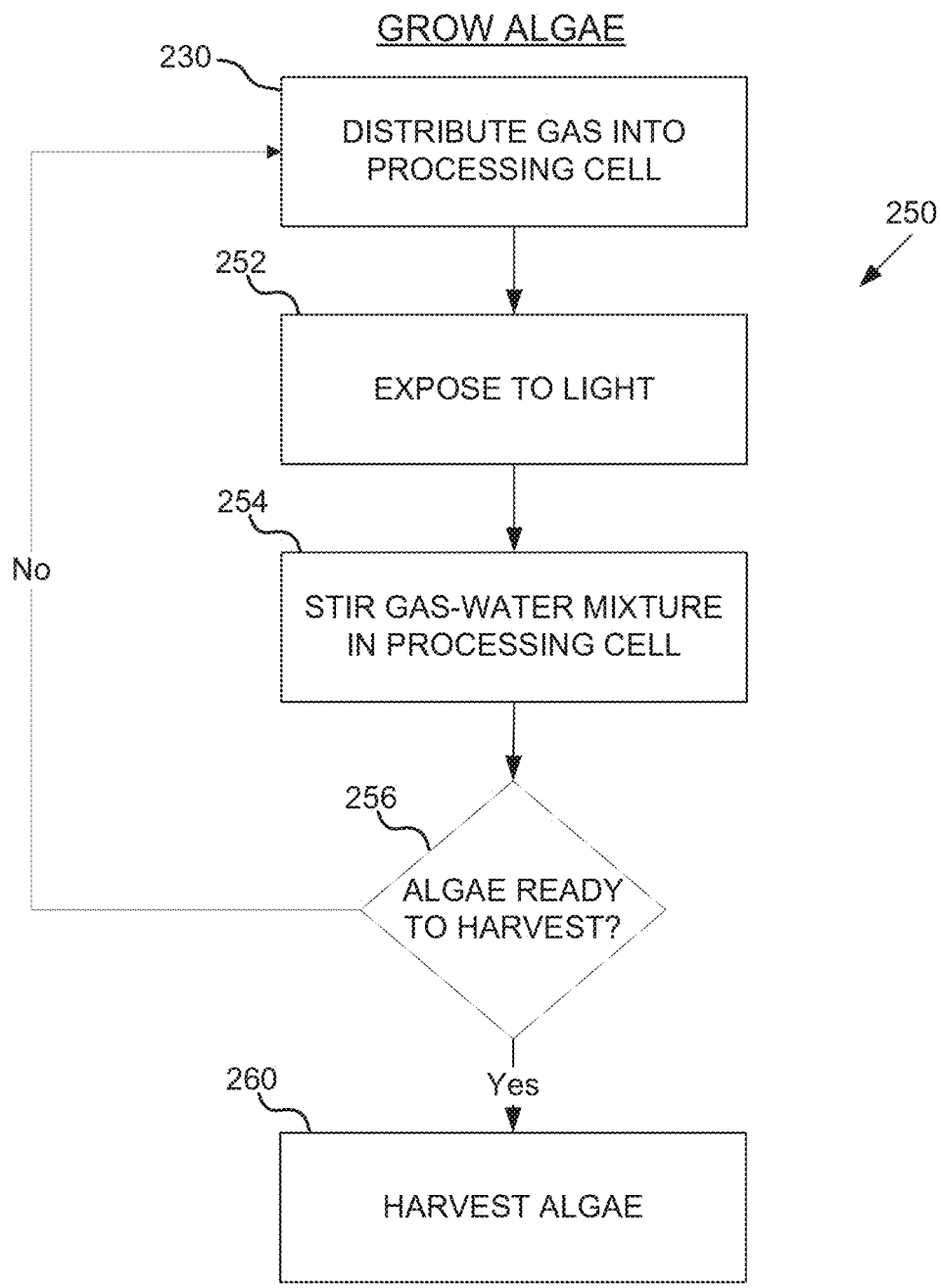
FIG. 2E is a process flow diagram illustrating a method for growing algae as part of a process for recycling flue gas.

FIG. 2E is a process flow diagram illustrating a method for growing algae as part of a process for recycling flue gas. Referring now to FIG. 2E, a method for growing algae comprises exposing the mixture of water, gas, lipid trigger, and nutrients to light at step 252, stirring the mixture at step 254, and determining if the algae is ready to harvest at step 256. For example, referring again to FIG. 1, the exposing to light of the mixture contained in processing cell 101 may include sub-steps performed by light emitting columns 156. Further, the stirring of the mixture contained in processing cell 101 may include sub-steps performed by moveable grate 150. In particular, moveable grate 150 may be moved up or down by adjusting buoyancy, wherein the buoyancy may be adjusted by adjusting the water-to-air ratio in ballast tanks 110. The determining of whether the algae is ready to harvest at step 256 may be accomplished through manual inspection, electronic sensors, a computer program or module, timing of anticipated growth intervals, or other means that may be known to one of ordinary skill in the art.

Figure 2F:
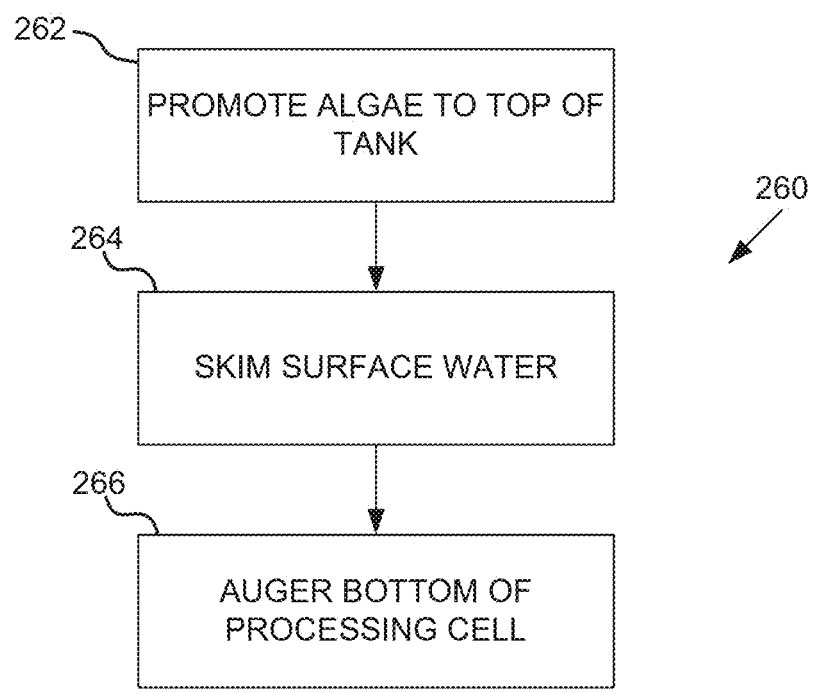
FIG. 2F is a process flow diagram illustrating a method for harvesting algae as part of a process for recycling flue gas.

FIG. 2F is a process flow diagram illustrating a method for harvesting algae as part of a process for recycling flue gas. Referring to FIG. 2F, a method for harvesting algae comprises promoting algae to the top of the processing cell at step 262 and skimming the surface of the water contained within the processing cell at step 264. For example, referring again to FIG. 1, promoting the algae to the top of the processing cell 101 may include sub-steps that are performed by gas bubblers 370. In particular, gas bubblers 370 comprise gas bubble valves that may be adjusted to release the gas-water mixture into the processing cell at an increased rate, thus creating an upward current surge and forcing the solid algae to the water surface where it may be skimmed. In some embodiments, solid matter that may fall to the bottom of processing cell 101 may be removed using an auger system at step 266.

In many embodiments, the harvested algae is evaluated for size. Algae that is more plump will usually contain more bio-oil. These larger, plump algae may be separated from the smaller, less plump algae, and the smaller algae may be re-introduced to a processing cell to continue growth and bio-oil production. The larger algae may be processed by separating the lipids contained inside the algae from the algae shell. The algae shell may then be used for as feedstock, or may be reintroduced as nutrients through the nutrients infuser. The lipids, or bio-oil, may then be processed and converted to biofuel, bioplastic, pharmacological products, or other bio-chemical products.

Figure 2G:
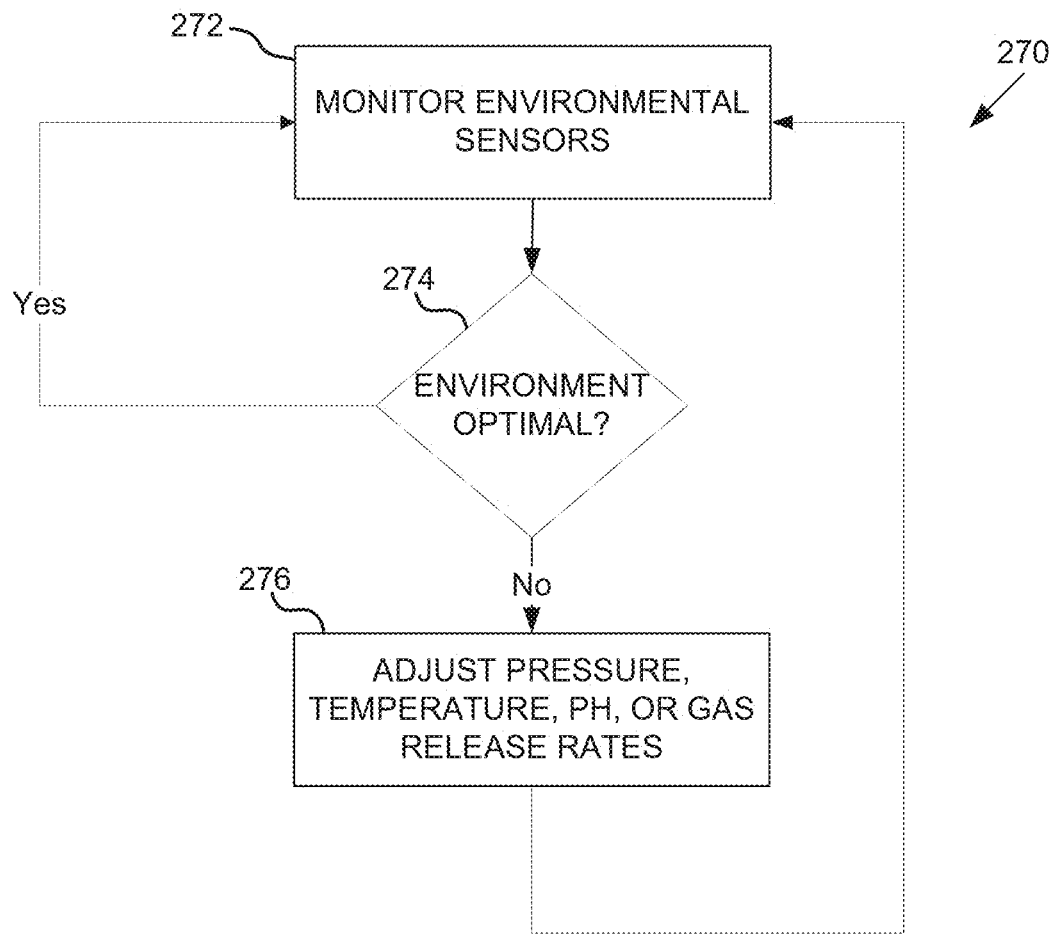
FIG. 2G is a process flow diagram illustrating a method for monitoring environmental variables of a flue gas recycling system.
Figure 6:
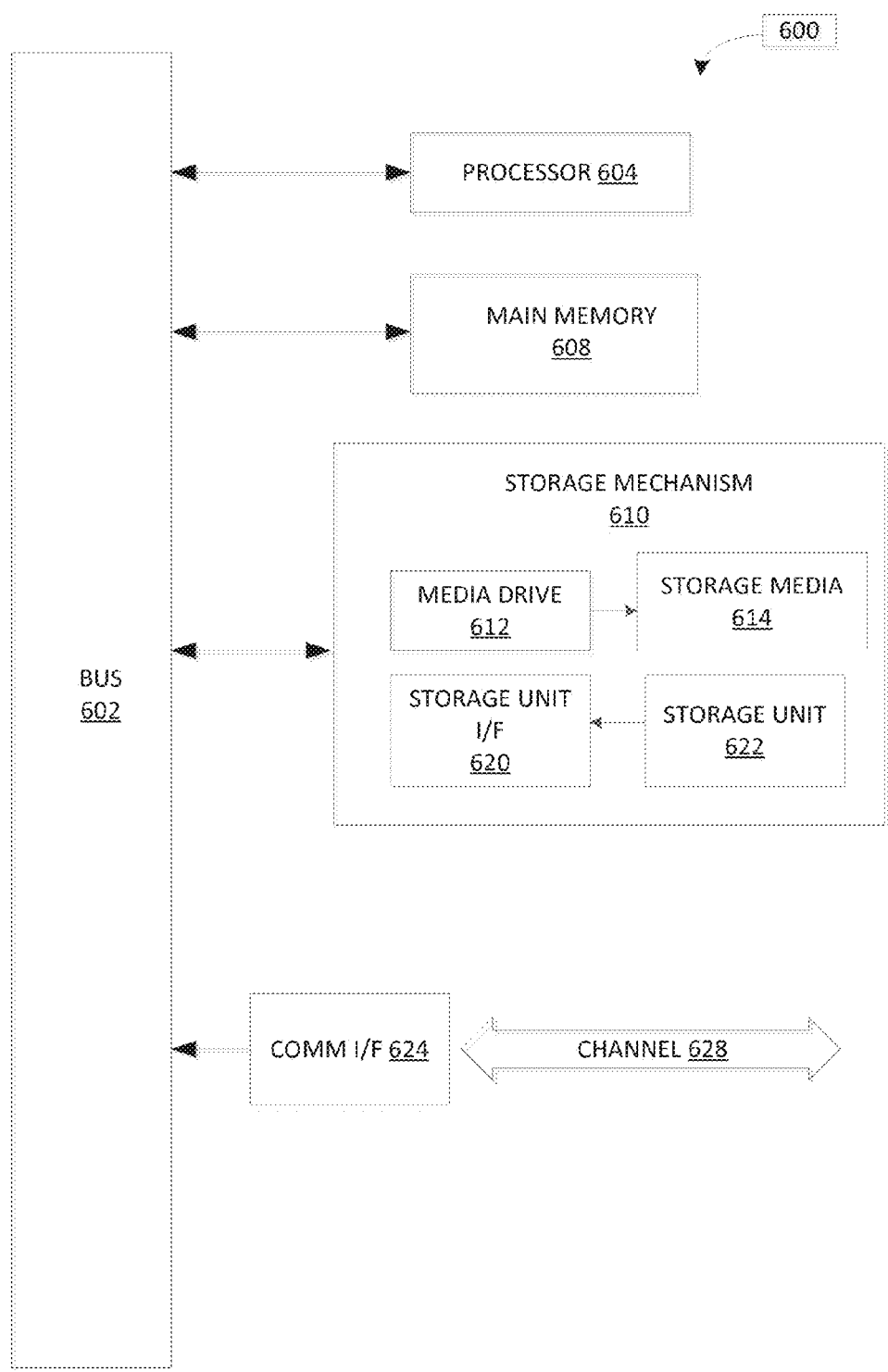
FIG. 6 illustrates an example computing module that may be used to implement various features of the systems and methods disclosed herein.

FIG. 2G is a process flow diagram illustrating a method for monitoring environmental variables of a flue gas recycling system. Referring now to FIG. 2G, monitoring environmental variables comprises monitoring sensors at step 272, comparing to optimal environmental settings at step 274, and adjusting environmental controls at step 276. For example, referring now to FIG. 3, monitoring environmental sensors may include sub-steps performed by monitoring environmental sensors 312, 352, and 354. Determining of optimal environmental conditions may be manually observed, or performed by computer programmable media as illustrated in FIG. 6. Referring again to FIG. 3, adjusting of environmental conditions may include sub-steps performed by adjusting heat exchanger 310 settings, adjusting pressure control valve 350, adjusting gas bubbler 370 settings, or adjusting pressure release valve 410 settings.

FIG. 2H is a process flow diagram illustrating a method for exhausting or recycling gas from a flue gas processing system. Referring now to FIG. 2H, a method for exhausting or recycling gas from the flue gas processing system comprises monitoring pressure and $CO_2$ levels inside enclosure 100 at step 282, and selectably releasing gas into the atmosphere at step 290 or selectably returning gas to the gas distribution system at step 288. For example, referring again to FIG. 3, the monitoring of pressure and $CO_2$ levels may include sub-steps performed by environmental sensors 312, 352, and 354. In some embodiments, monitoring may also include sub-steps performed manually. Alternatively, monitoring may include sub-steps performed by computer readable media, as illustrated in FIG. 6. Referring again to FIG. 3, selectably returning gas to gas distribution system 300 or releasing gas into the atmosphere may include sub-steps performed by pressure release valve 410.

Figure 3:
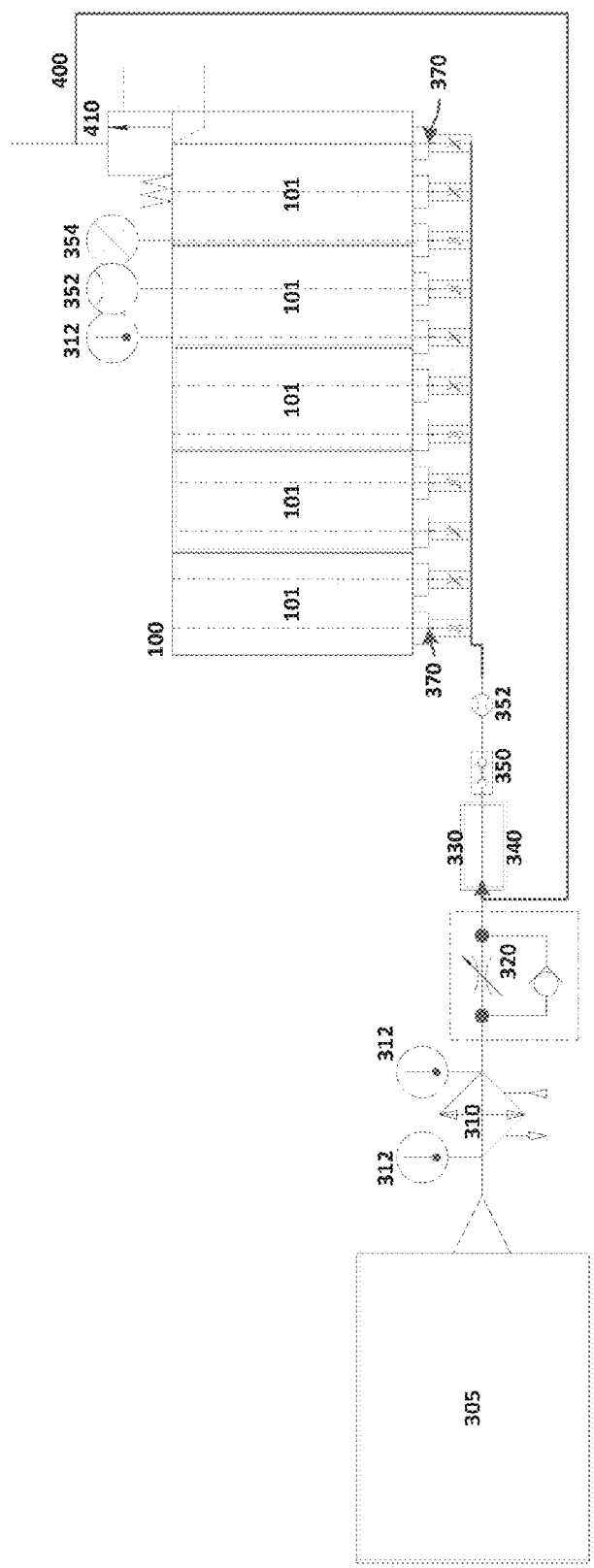
FIG. 3 is a cross-section diagram of a flue gas recycling system.

FIG. 3 is a cross-section schematic diagram of the gas distribution system 300 and the gas return system 400. Referring now to FIG. 3, the industrial plant's flue gas exhaust 305 pneumatically couples to the gas distribution system 300, the gas distribution system 300 pneumatically couples to the enclosure 100, and the enclosure 100 pneumatically couples to gas return system 400, wherein gas return system 400 also pneumatically couples to gas distribution system 300.

Still referring to FIG. 3, the gas distribution system may further comprise a heat reducing system 310 to reduce the heat of the flue gas such that gas released into the processing cells 101 are safe and conducive for algae growth. For example, the heat reducing system may be a heat exchanger. The gas distribution system may further comprise temperature sensors 312 to monitor temperature of the flue gas before and/or after being processed through the heat exchanger, as well as for monitoring the temperature within the cells and the enclosure to ensure that optimal growing conditions for the algae are maintained. Additionally, the gas distribution system may further comprise a backflow prevention system 320 to prevent water from the cells from flowing back through the gas distribution system and into the power plant's furnaces or other equipment. Notably, water may flow into and fill the gas distribution system from the cells 101 through the bubblers 370 all the way up to the backflow reduction system 320. Thus, water and flue gas may mix in the flooded parts of the gas distribution system. In some embodiments, the gas distribution system may further comprise a water holding tank to facilitate mixing of flue gas and water.

Still referring to FIG. 3, in some embodiments, the gas distribution system further comprises a pH control system 330. For example, the pH control system may use a limestone additive to adjust the pH of the water and $CO_2$ solution to safe and optimal levels for algae growth. Further, in some embodiments, the gas distribution system may also comprise a nutrients infusion system 340. The nutrients infusion system enables the addition of nutrients into the $CO_2$ solution to further stimulate algae growth and lipid production. In some exemplary embodiments, the nutrients infusion system is configured to introduce a lipid trigger into gas distribution system. The lipid trigger is an compound known to trigger algae to rapidly produce and store lipids. These lipids are the raw material that can be used to produce a biofuel that may be harvested from the algae.

Still referring to FIG. 3, in some embodiments the gas distribution system may further comprise flow control valve 350 and flow meter 352, enabling control of the overall rate at which flue gas is released into the enclosure. Additionally, the gas return system 400 may comprise pressure release valve 410 to controllably vent gas into the atmosphere or return gas to the gas distribution system 300. Temperature, pressure, $CO_2$ level, and other environmental sensors 312, 352, and 354 may be located at various positions within the enclosure to monitor environmental conditions. One example of possible positions for these sensors is illustrated in FIG. 3. Feedback from these sensors may be used to control environmental conditions in the flue gas recycling system. For example, the feedback data may be used to determine whether and how much gas is vented into the atmosphere as opposed to returned to the gas distribution system. For example, if detected $CO_2$ rates are relatively high, then more $CO_2$-rich gas may be returned to the gas distribution system, but if $CO_2$ rates are relatively low and $O_2$ rates are high, than more gas may be vented into the atmosphere. In addition, the feedback data may be used to control release rates of gas into specific processing cells, pH adjustments, and release rates of nutrients.

Figure 4:
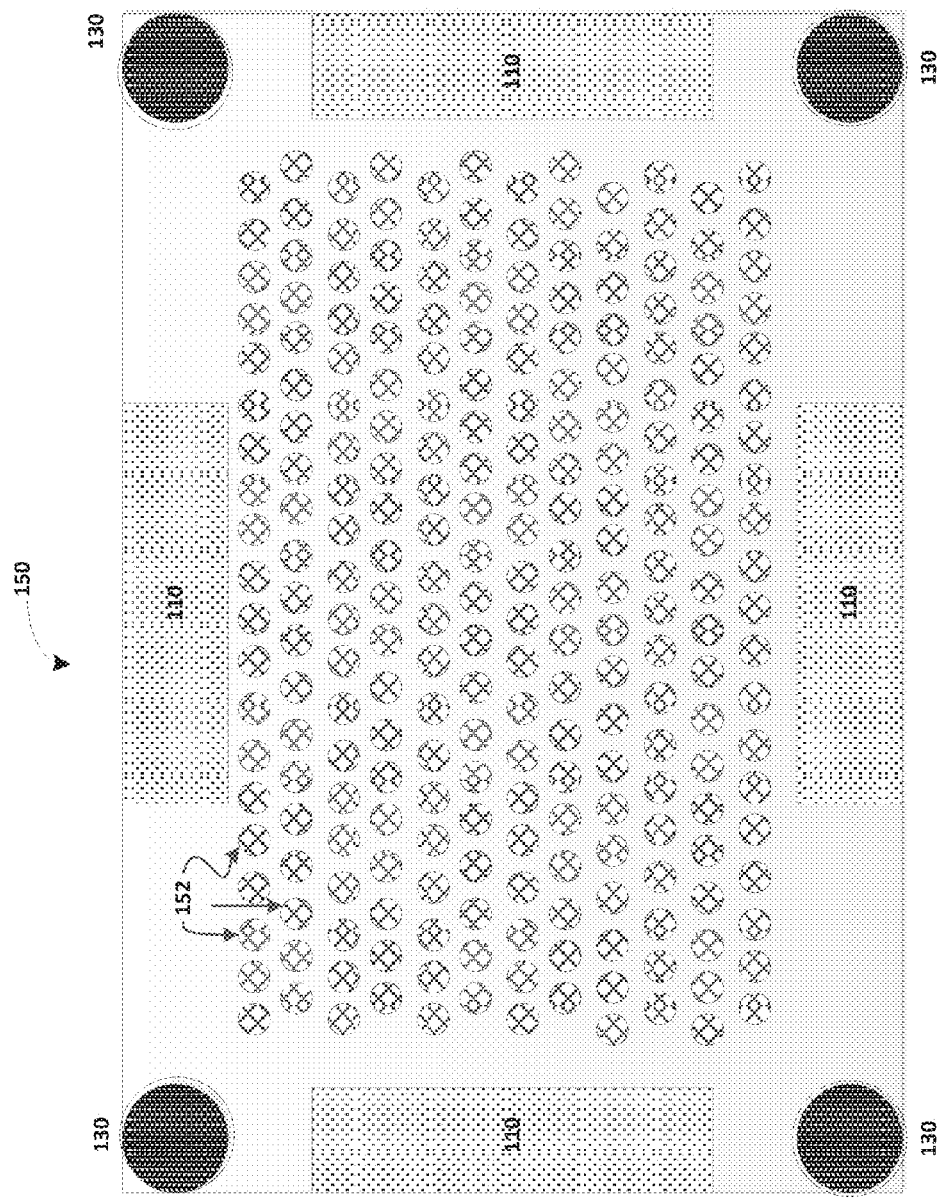
FIG. 4 illustrates a moveable grate from of a flue gas recycling system.

FIG. 4 is top-down view of a movable grate 150. Referring to FIG. 4, the grate comprises a plurality of ballast tanks 110 and a plurality of apertures 152. The apertures are shaped and positioned such that the light emitting columns will fit through the apertures with sufficient clearance to also enable water to flow through the grate when the grate moves up or down within the cell. Further, as discussed, the grate is slidably coupled to support columns 130 to guide the vertical movement of the grate caused by adjusting the levels of gas and water in ballast tanks 110. While FIG. 4 illustrates four support columns and four ballast tanks, it should be noted that other configurations are possible incorporating different varying quantities of ballast tanks and support columns. Further, the particular configuration, shape, and size of apertures 152 is shown for exemplary purposes only and different shapes, sizes, and configurations are possible and contemplated.

Figure 5:
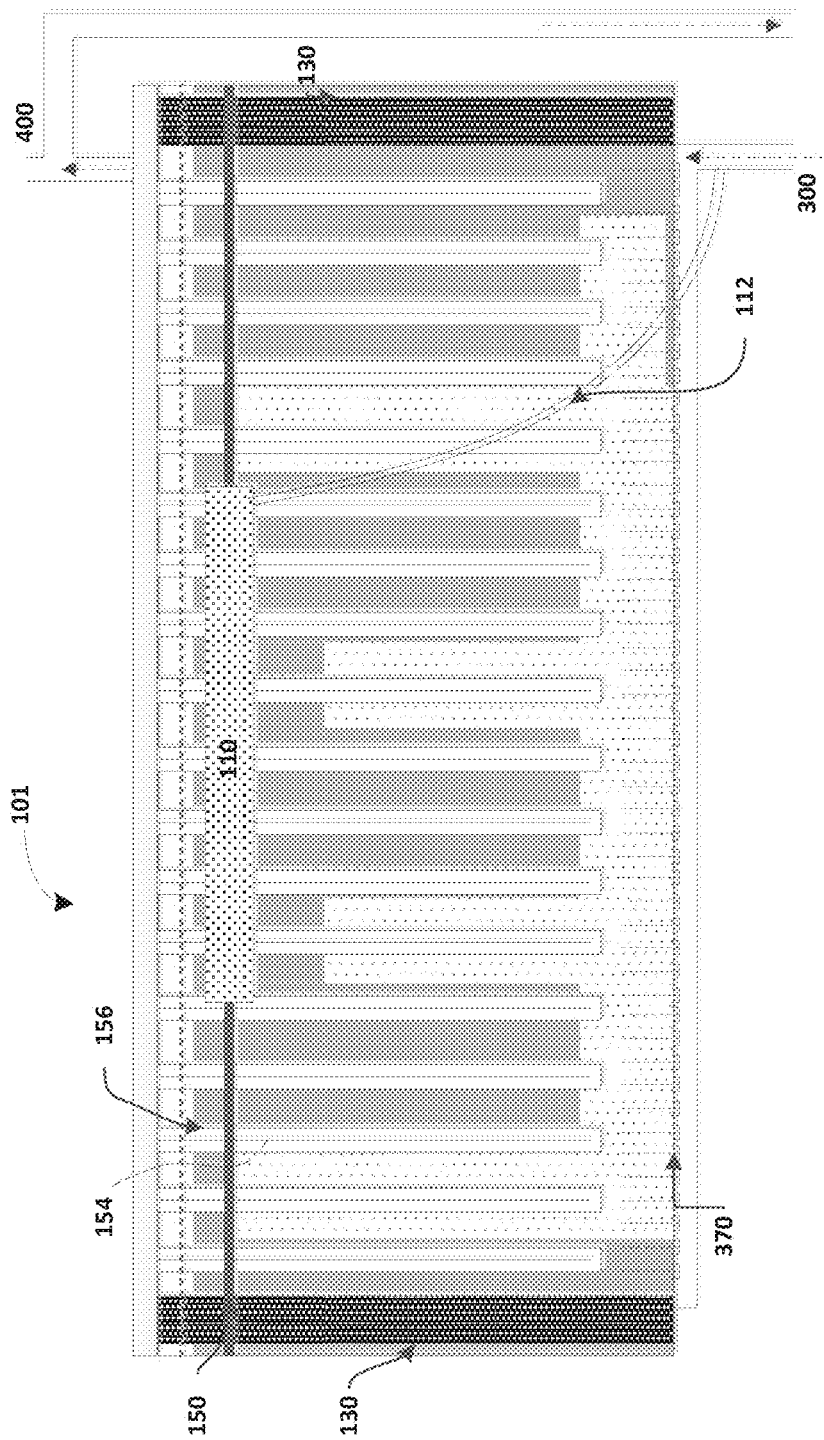
FIG. 5 illustrates a cross-section of a processing cell from a flue gas recycling system.

FIG. 5 is a cross-section diagram illustrating a cell 101. Referring to FIG. 5, ballast tanks 110 pneumatically couple to gas delivery system 200 through connector 112. This illustration further depicts an exemplary configuration of the cell wherein the moveable grate 150 is slightly below the surface of the water contained within the cell 101. However, as previously described, the grate's vertical position may be adjusted by varying the levels of gas and/or water in ballast tanks 110 to float or submerge the grate to desired depths.

In some embodiments, a mechanical or robotic skimmer may be utilized to harvest oil-rich algae. Algae may be promoted to the top of a particular cell by increasing the gas release rate from the bubblers coupled to that cell. In another exemplary embodiment, a compressed air tank or air compressor may be incorporated into the gas distribution system to further control the air pressure and allow for increased airflow through the system during algae harvest. Accordingly, the gas will push the algae to the top of the cell and a mechanical or robotic skimming device can be used to collect the algae. In one such example, the skimming device is a robotic floating device, similar to a floating pool sweep.

Many embodiments of the disclosure recite monitoring of environmental sensors, such as temperature, $CO_2$ or $O_2$ level, pH, pressure, and flow sensors, as well as adjusting multiple valve settings to control hydraulic and pneumatic flow or release rates. The monitoring of these sensors and adjustment of these controls may be accomplished manually or automatically. In either of these scenarios, computing modules and software may be utilized to accurately and efficiently enable control of optimal environmental conditions. For example, a computer processing module may be programmed to: (i) monitor the aforementioned environmental sensors, (ii) calculate optimal growing conditions for the algae based on data from the environmental sensors and known target conditions, and (iii) adjust settings on the heat exchanger, nutrients infuser, pH control system, bubblers, or any of the pressure release or flow valves to optimize and achieve those environmental conditions.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 6. Various embodiments are described in terms of this example-computing module 600. After reading this description, it will become apparent to a person skilled in the relevant art how to implement the application using other computing modules or architectures.

Referring now to FIG. 6, computing module 600 may represent, for example, computing or processing capabilities found within desktop, laptop, notebook, and tablet computers; hand-held computing devices (tablets, PDA's, smart phones, cell phones, palmtops, smart-watches, smart-glasses etc.); mainframes, supercomputers, workstations or servers; or any other type of special-purpose or general-purpose computing devices as may be desirable or appropriate for a given application or environment. Computing module 600 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 600 might include, for example, one or more processors, controllers, control modules, or other processing devices, such as a processor 604. Processor 604 might be implemented using a general-purpose or special-purpose processing engine such as, for example, a microprocessor, controller, or other control logic. In the illustrated example, processor 604 is connected to a bus 602, although any communication medium can be used to facilitate interaction with other components of computing module 600 or to communicate externally.

Computing module 600 might also include one or more memory modules, simply referred to herein as main memory 608. For example, preferably random access memory (RAM) or other dynamic memory, might be used for storing information and instructions to be executed by processor 604. Main memory 608 might also be used for storing temporary variables or other intermediate information during execution of instructions to be executed by processor 604. Computing module 600 might likewise include a read only memory ("ROM") or other static storage device coupled to bus 602 for storing static information and instructions for processor 604.

The computing module 600 might also include one or more various forms of information storage mechanism 610, which might include, for example, a media drive 612 and a storage unit interface 620. The media drive 612 might include a drive or other mechanism to support fixed or removable storage media 614. For example, a hard disk drive, a solid state drive, a magnetic tape drive, an optical disk drive, a CD or DVD drive (R or RW), or other removable or fixed media drive might be provided. Accordingly, storage media 614 might include, for example, a hard disk, a solid state drive, magnetic tape, cartridge, optical disk, a CD or DVD, or other fixed or removable medium that is read by, written to or accessed by media drive 612. As these examples illustrate, the storage media 614 can include a computer usable storage medium having stored therein computer software or data.

In alternative embodiments, information storage mechanism 610 might include other similar instrumentalities for allowing computer programs or other instructions or data to be loaded into computing module 600. Such instrumentalities might include, for example, a fixed or removable storage unit 622 and a storage interface 620. Examples of such storage units 622 and storage interfaces 620 can include a program cartridge and cartridge interface, a removable memory (for example, a flash memory or other removable memory module) and memory slot, a PCMCIA slot and card, and other fixed or removable storage units 622 and storage interfaces 620 that allow software and data to be transferred from the storage unit 622 to computing module 600.

Computing module 600 might also include a communications interface 624. Communications interface 624 might be used to allow software and data to be transferred between computing module 600 and external devices. Examples of communications interface 624 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 624 might typically be carried on signals, which can be electronic, electromagnetic (which includes optical) or other signals capable of being exchanged by a given communications interface 624. These signals might be provided to communications interface 624 via a channel 628. This channel 628 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 608, storage unit 620, media 614, and channel 628. These and other various forms of computer program media or computer usable media may be involved in carrying one or more sequences of one or more instructions to a processing device for execution. Such instructions embodied on the medium are generally referred to as "computer program code" or a "computer program product" (which may be grouped in the form of computer programs or other groupings). When executed, such instructions might enable the computing module 600 to perform features or functions of the present application as discussed herein.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

The invention claimed is:

1. A method for recycling flue gas comprising;
   accepting a flue gas into a flue gas recycling system, the flue gas recycling system comprising a gas distribution system, an air tight enclosure, a gas return system, and one or more processing cells encapsulated within the air tight enclosure, wherein the gas distribution system pneumatically couples to each processing cell through a plurality of bubblers, and
   the gas return system pneumatically couples the air-tight enclosure to the gas distribution system through a pressure release valve;
   cooling the flue gas prior to entering the plurality of bubblers;
   mixing the cooled flue gas with water prior to entering the one or more processing cells to create a gas-water mixture;
   distributing the gas-water mixture through the plurality of bubblers into the one or more processing cells;
   introducing a $CO_2$-breathing organism into the gas-water mixture distributed in the one or more processing cells;
   radiating light energy through the gas-water mixture;
   stirring the gas-water mixture inside the processing cell using a stirring mechanism;
   monitoring pressure and $CO_2$ levels inside the air-tight enclosure; and
   selectively venting the gas from the air-tight enclosure or returning the gas to the gas distribution system.

2. The method of claim 1, wherein cooling the flue gas comprises flowing the flue gas through a heat exchanger within the gas distribution system and the radiating light energy through the gas-water mixture comprises emitting light from a plurality of light-emitting columns located within the processing cell.

3. The method of claim 1, wherein mixing the flue gas with water comprises injecting the flue gas through a backflow prevention system prior to the plurality of bubblers and the stirring mechanism comprises a moveable grate and a plurality ballast tanks configured to cause the moveable grate to articulate vertically inside the processing cell.

4. The method of claim 1, further comprising adjusting a pH level of the gas-water mixture using a pH control system located within the gas distribution system between a backflow preventer and a plurality of bubblers.

5. The method of claim 4, wherein adjusting the pH level of the gas-water mixture further comprises exposing the gas-water mixture to limestone.

6. The method of claim 1, further comprising infusing the gas-water mixture with nutrients by controllably releasing nutrients from a nutrients infuser located within the gas distribution system between a backflow preventer and the plurality of bubblers.

7. The method of claim 6, further comprising infusing the gas-water mixture with a lipid trigger dispensed from the nutrients infuser.

8. The method of claim 1, further comprising controllably introducing compressed air into the gas-water mixture from a compressed air insertion system pneumatically coupled to the gas distribution system.

9. The method of claim 1, further comprising determining a $CO_2$ level in the processing cell, comparing the $CO_2$ level in the processing cell to a predetermined $CO_2$ level for optimal growth of the $CO_2$-breathing organism; and controllably increasing a release rate of gas-water mixture through a plurality of bubblers if the $CO_2$ level in the processing cell is below the predetermined $CO_2$ level for optimal growth of the $CO_2$-breathing organism.

10. The method of claim 1, further comprising determining a nutrients level in the processing cell, comparing the nutrients level in the processing cell to a predetermined nutrients level for optimal growth of the $CO_2$-breathing organism, and controllably increasing a release rate of nutrients from a nutrients infusion system if the nutrients level in the processing cell is below the predetermined nutrients level for optimal growth of the $CO_2$-breathing organism.

11. The method of claim 1, further comprising determining a lipid trigger level in the processing cell, comparing the lipid trigger level in the processing cell to a predetermined lipid trigger level for optimal bio-oil production by the $CO_2$-breathing organism, and controllably increasing a release rate of a lipid trigger from a nutrients infusion system if the lipid trigger level is below the predetermined lipid trigger level for optimal bio-oil production by the $CO_2$-breathing organism.

* * * * *